(12) United States Patent
Scheurer

(10) Patent No.: US 8,834,567 B2
(45) Date of Patent: Sep. 16, 2014

(54) MIDDLE EAR PROSTHESIS HAVING DISCRETE PROJECTIONS FOR PURPOSES OF OSSICULAR ATTACHMENT

(76) Inventor: Mark Matthew Scheurer, Coronado, CA (US)

( * ) Notice: Subject to any disclaimer, the term of this patent is extended or adjusted under 35 U.S.C. 154(b) by 204 days.

(21) Appl. No.: 13/524,515

(22) Filed: Jun. 15, 2012

(65) Prior Publication Data
US 2013/0053957 A1    Feb. 28, 2013

Related U.S. Application Data

(60) Provisional application No. 61/529,590, filed on Aug. 31, 2011.

(51) Int. Cl.
*A61F 2/18* (2006.01)
(52) U.S. Cl.
CPC ........... *A61F 2/18* (2013.01); *A61F 2220/0016* (2013.01); *A61F 2002/183* (2013.01)
USPC ........................................................ 623/10
(58) Field of Classification Search
CPC ................ A61F 2/18; A61F 2002/183; A61F 2220/0008; A61F 2220/0016; A61F 2310/00796; A61F 2310/00928; A61F 2310/00952
USPC .......................................................... 623/10
See application file for complete search history.

(56) References Cited

U.S. PATENT DOCUMENTS

| | | | | |
|---|---|---|---|---|
| 5,104,401 | A * | 4/1992 | Kurz | 623/10 |
| 6,579,317 | B2 * | 6/2003 | Kurz | 623/10 |
| 7,628,812 | B2 | 12/2009 | aWengen et al. | |
| 2007/0055372 | A1 * | 3/2007 | Prescott et al. | 623/10 |
| 2008/0097603 | A1 * | 4/2008 | Brosnahan et al. | 623/10 |
| 2008/0208338 | A1 | 8/2008 | Eiber et al. | |
| 2009/0317766 | A1 * | 12/2009 | Heidenau et al. | 433/201.1 |

FOREIGN PATENT DOCUMENTS

WO    2008/027862 A2    3/2008

OTHER PUBLICATIONS

International Search Report dated Nov. 4 2012, from PCT Application PCT/US12/51493 filed on Aug. 17, 2012 which claims the benefit of U.S. Appl. No. 13/524,515, with the citations from the ISR: DE102007008851 (US20080208338), WO 2008027862 A2 (US 20080058927), and SU 1001922 A1.
Written Opinion dated Nov. 4 2012, from PCT Application PCT/US12/51493 filed on Aug. 17, 2012 which claims the benefit of U.S. Appl. No. 13/524,515.

* cited by examiner

*Primary Examiner* — Andrew Iwamaye
(74) *Attorney, Agent, or Firm* — Daniel A. Tanner, III; PRASS LLP

(57) ABSTRACT

A middle ear ossicle prosthesis in which the component for ossicular attachment comprises a surface bearing a plurality of discrete projections facing the ossicle to which it is attached which minimize total contact between the prosthesis and the ossicle. The prosthesis may comprise a loop forming a partial circle for encircling an ossicle, a piston for transmitting vibrations from the loop to the inner ear, and a rod solidly connecting the loop to the piston. The loop may have an upwardly turned end to facilitate placement of the loop over the ossicle. The projections may be provided in one row, two rows, or may be otherwise arrayed, and may be dissimilar from one another in configuration and dimensions.

15 Claims, 2 Drawing Sheets

MIDDLE EAR PROSTHESIS HAVING DISCRETE PROJECTIONS FOR PURPOSES OF OSSICULAR ATTACHMENT

CROSS-REFERENCE TO RELATED APPLICATION

This application claims priority benefit of Application No. 61/529,590, filed Aug. 31, 2011.

BACKGROUND OF INVENTION

Numerous prior designs of ossicular prostheses have sought to establish functional continuity of the ossicular chain after damage to some or all of the ossicles secondary to disease or congenital anomaly. Frequently, when the stapes is damaged or diseased, re-establishment of a connection to the inner ear via stapedectomy or stapedotomy is also required. Prostheses most often are designed to attach to remaining healthy ossicles and replace the function of the ossicle(s) which are missing or diseased.

In the case of the stapes, dysfunction often occurs as a result of a disease process called otosclerosis in which the footplate of the stapes becomes fused to the surrounding bone and no longer effectively transmits ossicular motion to the fluids of the inner ear. Most stapes prostheses over the last several decades have been constructed of either a circumferential or nearly circumferential wire loop or a broader ribbon-type (flat wire) loop which directly attaches to the long process of the incus. More recently, clip-type prostheses have been developed which are comprised of a complex-shape broad ribbon in which a more limited surface area of the incus is placed in contact with the flattened clip. In either case, the component for incus attachment is joined to a piston which fits into a hole (fenestra) in the stapes footplate created by the surgeon so that the piston can translate ossicular movement to the fluids of the inner ear.

Ossicular prostheses which have been designed to replace the function of the stapes and attach to the incus have frequently caused necrosis/erosion (loss of bone tissue) in the area of the incus to which they are attached, as well as the bone more distal to the prosthesis attachment. This bone loss in the area of the prosthesis attachment can cause loosening of the prosthesis and resultant hearing loss because of piston migration out of the hole in the stapes footplate and/or decoupling of the motion from the incus to the prosthesis. Ideally, the ossicular prosthesis which is designed to replace the function of the stapes will attach firmly and permanently to the long process of the incus without ever loosening or migrating away from its position of placement at the time of surgery. This is also true of prostheses which attach to the malleus and replace the function of the other ossicles.

Bone/tissue loss in the area of the attachment of the stapes prosthesis to the incus is thought to be due to impaired blood supply to the long process of the incus after surgery. Prior to surgery, blood is supplied to the area of the long process from both the body of the incus distally to the long process, as well as from the opposite direction across the joint where the incus is joined to the stapes. Since the attachment between the stapes and incus is cut during surgery, the only blood supply to the long process of the incus after surgery flows distally to the long process from the body of the incus. Accordingly, blood flow to supply the area of the incus both at and distal to the prosthesis attachment ideally should not be restricted by the prosthesis itself. It is widely believed that a prosthesis which exerts sufficient mechanical pressure on blood vessels/ mucosa near the surface of the incus can cause a restriction of blood flow sufficient to cause incus necrosis and subsequent failure of the prosthesis.

Since the blood supply in the area of the prosthesis attachment is tenuous after surgery and most prostheses have areas of very broad or circumferential contact points with the long process, relatively large areas where blood vessels or delicate mucosa are located can be compressed by the prosthesis and cause death of the underlying or distal tissues. Efforts to reduce both the amount and the surface area of mechanical pressure exerted on the incus have resulted in new prostheses with broader and/or softer ribbons to contact the incus; new methods of crimping to achieve optimal pressure on the incus (tight enough to ensure good coupling of incus translation to that of the piston in the inner ear, but loose enough to reduce the chance of pressure necrosis); or a change in the shape of the ribbon or wire so that only opposing sides of the incus are grasped firmly. Nevertheless, all efforts to date share the common characteristic that at least some of the wire or ribbon is broadly in contact with the incus and consequently have the potential to cause pressure necrosis to the underlying mucosa and loss of bone in these areas of broad contact.

In the case of prostheses which attach to the malleus to replace the function of the incus, stapes, or both, the prosthesis most often is placed in contact with the medial portion of the malleus. Contact is not usually made with the lateral aspect of the malleus because its lateral surface is integrated with the ear drum. The prosthesis component which contacts the malleus usually comprises a flat disc with a shallow depression in which the medial malleus lies. Commonly, the prosthesis "falls over" after surgery with a loss of contact with the malleus, with resultant hearing loss. Continuing malleus-prosthesis contact after surgery is initially dependent solely on the medial pressure the malleus exerts on the prosthesis.

SUMMARY

The present invention relates to the concept that if a relatively large patch or area of contact between an ossicular prosthesis and an ossicle can be avoided, then disturbance to the underlying mucosa and blood vessels can be minimized with a reduction in the chance for necrosis. More particularly, broad contact may be minimized by a design in which discrete projections from the prostheses' ossicle interface surface space that surface away from the bone. Moreover, a very secure attachment between the ossicle and the prosthesis can be anticipated, due to the resistance to motion engendered by the partial embedment of these projections in the ossicle. A more secure attachment can be anticipated to reduce the chance of prosthesis translocation following surgery, which can cause surgical failure even in the absence of ossicular necrosis.

It is an object of the invention to provide novel means of attachment for an ossicular prosthesis to an ossicle using a plurality of projections extending from a wire, loop, ribbon, clip, disc, or other prosthesis surface form or configuration which would serve as contact points between the ossicle to which they are attached and the prosthesis from which they arise.

The projections can be of variable number, shape, length and arrangement according to the intended use in a particular patient's anatomy and disease process.

The projections are inherently designed to minimize the surface area of prosthesis to ossicle contact, thereby minimizing the potentially damaging effect that broader contact may have, as described in "Background of the Invention." They also have the advantage of attaching firmly to the ossicle via embedment of said projections which is anticipated to reduce the risk of surgical failure further by reducing the risk the prosthesis will move away from its position at the time of surgical implantation.

In one embodiment, the projections are envisioned as having sharp ends which could enhance firm embedment in the ossicular bone to which they are in contact, creating a secure attachment without a significant amount of total contact between the prosthesis and the ossicle.

In accordance with one embodiment of the invention, the prosthesis could be comprised of metal such as titanium with projections as described consisting of a different substance, such as hydroxyapatite which could fully integrate with underlying bone.

BRIEF DESCRIPTION OF THE DRAWINGS

The drawings, when considered in connection with the following description, are presented for the purpose of facilitating an understanding of the subject matter sought to be protected.

DETAILED DESCRIPTION

Figure 1:
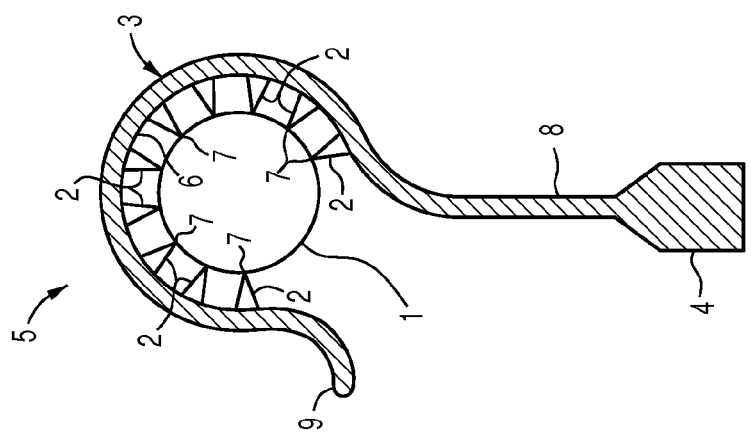
FIG. 1 is a side view, not drawn to scale, of a prosthesis according to at least one aspect of the invention.

FIG. 1 shows a middle ear prosthesis such as a stapes prosthesis 5 comprising a loop 3 which is formed as a partial circle of at least one hundred eighty degrees, or as shown, three hundred to three hundred thirty degrees, for encircling an ossicle such as an incus 1 (seen in cross section in FIG. 1). It would of course be possible to arrange the loop 3 as a full circle, by adding an element which closes the gap which exists when the loop 3 forms a partial circle as depicted and a suitable fastener for retaining the added element to the loop 3 (this option is not shown). The loop 3 bears a linear array of projections or spikes 2, which may for example be arrayed as a row of spikes 2, which project inwardly from the inner surface 6 of the loop 3, and which make contact with the underlying incus 1. The terms projection and spike, both in the singular and in the plural, will be used interchangeably herein. Inwardly signifies towards the center of the circle which would exist if the loop described a full circle. The surface 6 may be flat, curved, or complex. The loop 3 is attached by a rod 8 to a piston 4 which sits in a fenestra (not shown) and communicates with the inner ear so as to pass vibrations in a manner approximating that which would occur should all of the ossicles be functioning normally. It will be seen that only the points 7 of the spikes 2 make contact with the incus 1. This limits the patch of contact between the prosthesis 5 and the incus 1 which would otherwise broadly occur with the inner surface 6. The piston 4 is coupled to and terminates the rod 8.

The loop 3 may take various forms, such as a wire, ribbon, loop, or clip, disc, or other configurations.

The loop 3 may comprise an upturned end 9 located at that end of the loop 3 which is opposite the rod 8. The upturned end 9 may form an angle of greater than 90 degrees (not shown), which would enable the jaws of a clamp to both distract and compress the loop during placement or removal of the loop on an ossicle. The loop 3, the piston 4, and the rod 8 may be formed from a biocompatible material such as titanium or an alloy thereof. The spikes 2 may be formed from a material which simulates bone tissue, such as hydroxyapatite. Hydroxyapatite is desirable as it can fuse readily to natural bone tissue.

Figure 2:
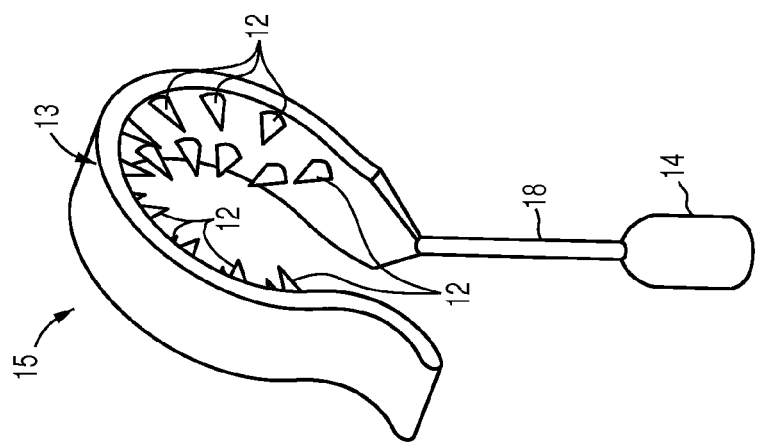
FIG. 2 is a perspective view of a prosthesis according to at least one other aspect of the invention.

FIG. 2 is a perspective view of a stapes prosthesis 15 according to at least one other aspect of the invention. The ossicle to which the stapes prosthesis 15 is engaged is omitted in FIG. 2 for clarity of the view. In the stapes prosthesis 15, a loop 13 which generally corresponds in function and structure to the loop 3 of FIG. 1 is sufficiently broad so as to bear two rows of spikes 12. The spikes 12 may be similar in function and structure to the spikes 2 of FIG. 1. Provision of two rows of spikes 12 increases the area of the ossicle such as the incus 1 of FIG. 1 which serves as a support surface for the stapes prosthesis 15, thereby increasing stability of contact over the single row of spikes 2 seen in FIG. 1. Other than the spikes 12, the stapes prosthesis 15 may be similar in structure and function to the stapes prosthesis 5 of FIG. 1, such as by including a piston 14 and a rod 18, which may be the structural and functional equivalents of the piston 4 and the rod 8 of FIG. 1.

As depicted in FIG. 2, the rows of spikes 12 are staggered in that when viewed from the end as illustrated in FIG. 1, all of the spikes 12 would be seen because those spikes 12 farther from the observer may be located between adjacent spikes 12 of the row relatively closer to the observer. However, the spikes 12 may be disposed abreast of one another, or alternatively stated, not staggered if desired.

Figure 3:
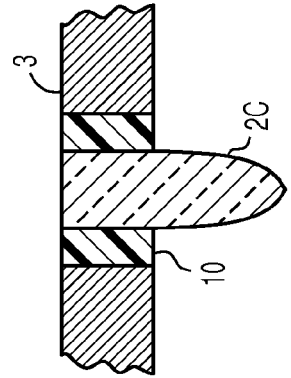
FIG. 3 is a cross sectional detail side view of a prosthesis according to a further aspect of the invention, and is drawn to enlarged scale.

FIG. 3 shows further features of the invention. These features will be described in terms of the stapes prosthesis 5 of FIG. 1, but will be understood to apply to any prosthesis according to the present invention. In one feature, a discrete projection 2A from the loop 3 may differ in length (called out by the reference numeral L1) and shape from the length (called out by the reference numeral L2) and shape of another spike 2B. The shape of the spike 2A may be somewhat bullet shaped, whereas the shape of the spike 2B may be substantially triangular. Of course, other shapes and dimensions may be substituted for those explicitly shown and described herein.

Figure 4:
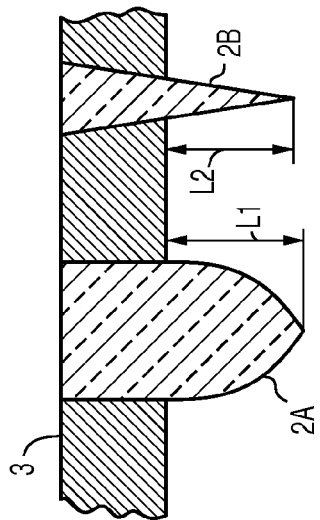
FIG. 4 is a cross sectional side view of a detail of a prosthesis according to still another aspect of the invention, and is drawn to enlarged scale.

FIG. 4 shows still another feature of the invention, and again, will be described in terms of the stapes prosthesis 5 of FIG. 1, but will be understood to apply to any prosthesis according to the present invention. A transition substance 10 may be disposed between the loop 3 and the spikes, such as a spike 2C. This transition substance 10 may be a substance other than the constituent substance of the loop and the constituent substance of the spikes. For example, the transition substance 10 may be a polymeric material including a shape memory polymeric material or a metal including shape memory metal. Shape memory materials are those which assume their original configuration after forces which deform the object made from shape memory materials are removed. Heat or other influences may be necessary to return a shape memory material object to its original configuration. Nitinol is an example of a shape memory metal which may be employed. Should assembly of the stapes prosthesis 5 deform the spikes 2, upon disassembly and with heat or other necessary influences supplied, the spikes 2 will reassume their original configuration. For example, should assembly cause the spikes 2 to bend from an original perpendicular orientation relative to the loop 3, if fabricated from shape memory materials they will reassume the original perpendicular orientation when disassembled and heated if necessary to invoke the shape memory feature.

While the discrete projections such as the spikes 2 have been described and shown as being tapered, there is no requirement that they be tapered in order to accomplish their mission of causing the loop of the prosthesis such as the loop 3 to be spaced apart from the bone such as the incus 1. The projections may be cylindrical or flattened for example, with or without points such as the points 7.

A prosthesis utilizing the attachment element shown in the stapes prosthesis 5 may be used to secure a foreign body such as a magnet to an ossicle. The foreign body may perform a role of assisting in hearing, as is known in the art. The foreign body may comprise a magnet which is subjected to electrical or magnetic pulses so as to vibrate.

Figure 5:
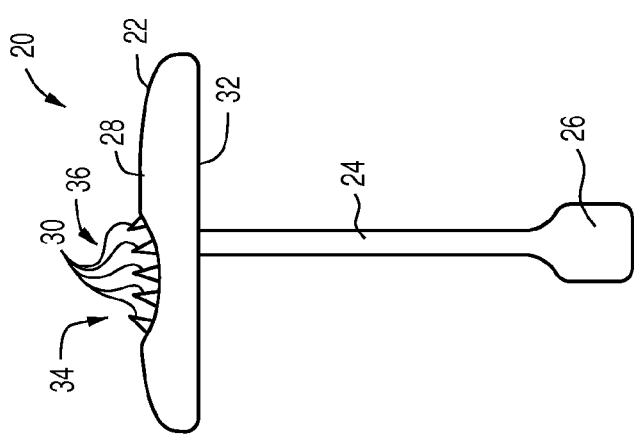
FIG. 5 is a side view, not drawn to scale, of a second embodiment of a prosthesis according to the present disclosure.

FIG. 5 shows an ossicular prosthesis 20 having an enlarged head 22 which may be attached by a rod 24 to a piston 26. The piston 26 may sit in a fenestra (not shown) and communicate with the inner ear so as to pass vibrations in a manner approximating that which would occur should all of the ossicles be undamaged. Alternatively, the rod may connect to another attachment element for fixation to another ossicle. The enlarged head 22 may generally assume the configuration of a disc having a first principal face 28 bearing projections 30 which may be the structural and functional equivalents of the projections or spikes 2 and 12 of FIGS. 1 and 2, respectively. An opposed principal face 32 is that from which the rod 24 projects. The rod serves as a vibration transmission element. The enlarged head 22 may have formed therein a recess 34 which is dimensioned and configured to seat an ossicle of the middle ear and which comprises a surface 36 from which the projections 30 project. The surface 36 may be curved and concave as shown.

Figure 6:
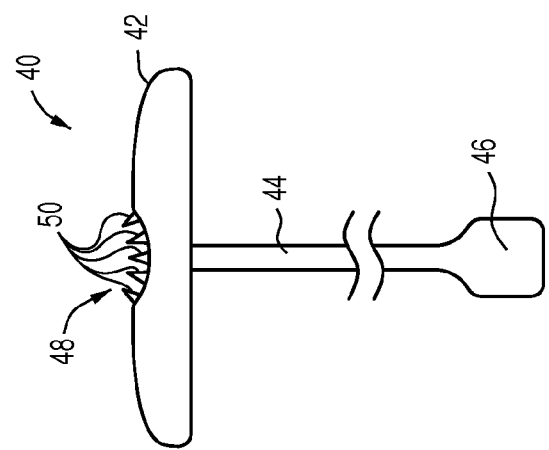
FIG. 6 is a side view, not drawn to scale, of a third embodiment of a prosthesis according to the present disclosure.

Several variations of the enlarged head are possible. One variation is shown in FIG. 6, which shows an ossicular prosthesis 40 having an enlarged head 42 which may be attached by a rod 44 to a piston 46. The enlarged head 42 may bear a recess 48 which may be centered on the enlarged head 42 in at least one view as seen, and which, apart from its location relative to the enlarged head 42 may be the structural and functional equivalent of the recess 34 of the prosthesis 20. The recess 48 may bear projections 50 which may be the structural and functional equivalents of the projections 30 of the ossicular prosthesis 20.

Figure 7:
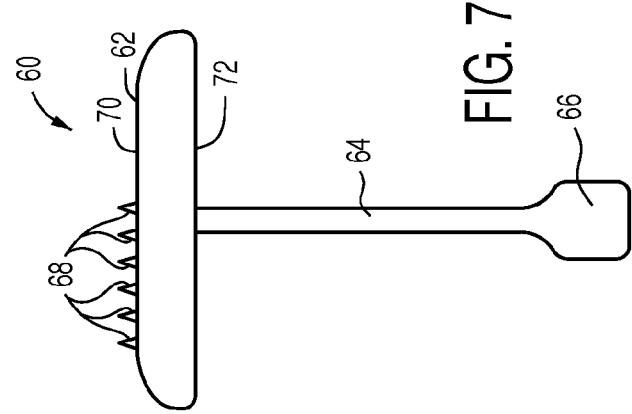
FIG. 7 is a side view, not drawn to scale, of a fourth embodiment of a prosthesis according to the present disclosure.

A further variation is shown in FIG. 7, which depicts an ossicular prosthesis 60 having an enlarged head 62 which may be attached by a rod 64 to a piston 66 or an attachment element for another ossicle (not shown). Unlike the prostheses 20 and 40, the prosthesis 60 does not have a recess. Rather, projections 68 are fixed directly to a first principal face 70, with the rod 64 being fixed to an opposed second face 72. The projections 68 may be arrayed as a patch or linear array located off center on the enlarged head 62 as shown, or if desired, may be centered on the enlarged head or may cover the entire enlarged head (these options are not shown).

It will be recognized that as employed herein, the term disc is intended only as a semantic convenience and should not be literally construed. The significance of a disc is that a disc presents two opposed principal or large faces among other surfaces, one which may support projections such as the projections 2, 12, 30, 50, and 68 and optionally, a recess such as the recesses 34 and 48, and the other of which supports or is coupled to the rod such as the rods 24, 44, and 64.

Regardless of the precise nature of a middle ear prosthesis according to the present invention, it will be understood to comprise an ossicular attachment element which is dimensioned and configured to engage an ossicle of the inner ear, such as the loop 3 or 13 or any of the enlarged heads 22, 42, and 62, a plurality of projections which project from the ossicular attachment element in a direction facing the ossicle being engaged, such as the projections 2, 12, 30, 50, and 68, and a vibration transmission element which is connected to the ossicular attachment element and dimensioned and configured to pass vibrations conducted from the projections to another ossicle or directly to the inner ear, such as any of the rods 8, 18, 24, 44, and 64. The projections such as the projections 2, 12, 30, 50, and 68 collectively define a discontinuous surface of dimensions and configuration to contact and engage the ossicle of the middle ear in a manner capable of supporting the middle ear prosthesis in operable position to transmit vibrations and maintain firm contact with the ossicle, while reducing the patch of contact between the prosthesis and the ossicle from that which would be present in the absence of the projections such as the projections 2, 12, 30, 50, and 68.

The vibration transmission element, which is in the above description provided by the rods 8, 18, 24, 44, and 64, may be devoid of a piston such as the pistons 4, 14, 26, 46, and 66, should the end of the rods be sufficient in dimensions and configuration to fulfill the function provided by the pistons. For example, rods may be tapered along their length and terminate in an end of dimensions greater than that at the enlarged head such as the loops 3 and 13, or the enlarged heads 22, 42, and 62.

It will be recognized by those of skill in the art that although the figures illustrate a loop stapes prosthesis and a principal/opposed principal face design which is most often used to attach to the malleus, other prostheses which attach to any of the ossicles may utilize the novel principles.

The invention may be thought of as the entire prosthesis, such as the stapes prostheses 5 and 15 or the prostheses 20, 40, and 60, or alternatively, as a substantial element of such a prosthesis. For example, the invention may be regarded as that portion of the stapes prosthesis 5 including the loop 3 and spikes 2, but may possibly not include the piston 4 or even the rod 8. If realized as a partial prosthesis, the invention may include a connector (not shown) enabling ready attachment of the rod 8, piston 4, or other members furthering the function of the inventive prosthesis.

While particular embodiments of the invention have been described, it is not intended that the invention be limited thereto. It is intended that the invention will be as broad in scope as the art will allow and that the application will be read likewise. Other embodiments for prostheses utilizing the attachment design described can be utilized in situations other than those involving attachment of a stapes prosthesis to the incus, or of the malleus to the stapes or stapes footplate. It can therefore be appreciated by those skilled in the art that other situations requiring secure attachment of a prosthesis to an ossicle can utilize the invention as claimed.

What is claimed is:

1. A middle ear prosthesis component, comprising:
   an ossicular attachment element having a loop, the loop being dimensioned and configured to at least partially encircle a first ossicle of the middle ear, and a plurality of discrete projections, each of the plurality of discrete projections
  (1) having an elongated axis that projects from a surface of the loop in a direction inwards through a region encompassed by the loop to face the first ossicle, and
  (2) having a free end configured to contact and engage the first ossicle in a manner that supports the middle ear prosthesis component in an operable position to transmit vibrations and to maintain contact with the first ossicle.

2. The middle ear prosthesis component of claim 1, further comprising a vibration transmission element that is operably connected to the ossicular attachment element and dimensioned and configured to pass vibrations conducted from the plurality of discrete projections to an inner ear.

3. The middle ear prosthesis component of claim 1, further comprising a vibration transmission element that is operably connected to the ossicular attachment element and dimensioned and configured to pass vibrations conducted from the plurality of discrete projections to a second ossicle via a second ossicular attachment element that is configured to engage a second ossicle.

4. The middle ear prosthesis component of claim 1, wherein the plurality of discrete projections collectively define a discontinuous contact surface with the first ossicle.

5. The middle ear prosthesis component of claim 1, wherein the plurality of discrete projections are formed of a different material than a material from which the ossicular attachment element is formed.

6. The middle ear prosthesis component of claim 1, wherein the plurality of discrete projections are formed of hydroxyapatite.

7. The middle ear prosthesis component of claim 1, wherein the ossicular attachment element from which the plurality of discrete projections project is formed, at least in part of one of a group of constituent materials including hydroxyapatite, polymer, metal, and nitinol.

8. The middle ear prosthesis component of claim 1, wherein a first one or more of the plurality of discrete projections have a first shape and a second one or more of the plurality of discrete projections have a second shape that is different from the first shape.

9. The middle ear prosthesis component of claim 1, wherein a first one or more of the plurality of discrete projections have a first length in a direction of projection from the ossicular attachment element and a second one or more of the plurality of discrete projections have a second length in the direction of projection from the ossicular attachment element, the second length being a different length than the first length.

10. The middle ear prosthesis component of claim 1, wherein the plurality of discrete projections are arranged in one row with bases of the plurality of discrete projections being in a single plane of projection from the ossicular attachment element.

11. The middle ear prosthesis component of claim 1, wherein the plurality of discrete projections are arranged in two or more rows with bases of the plurality of discrete projections being in more than one plane of projection from the ossicular attachment element.

12. The middle ear prosthesis component of claim 1, wherein the plurality of discrete projections are arranged in a linear pattern projecting from the ossicular attachment element.

13. The middle ear prosthesis component of claim 1, wherein the plurality of discrete projections are arranged in a staggered pattern projecting from the ossicular attachment element.

14. The middle ear prosthesis component of claim 1, further comprising a separate mechanical component, the separate mechanical component configured to be secured to the first ossicle via the ossicular attachment element and the plurality of discrete projections.

15. A middle ear prosthesis comprising:
an ossicular attachment element that is configured to engage an ossicle of the middle ear, the ossicular attachment element comprising:
  a loop being dimensioned and configured to at least partially encircle the ossicle,
  a plurality of discrete projections, each of the plurality of discrete projections
    (1) having an elongated axis that projects from a surface of the loop in a direction inwards through a region encompassed by the loop to face the ossicle to be engaged, and
    (2) having a free end configured to contact and engage the ossicle in a manner that supports the middle ear prosthesis in an operable position to transmit vibrations and to maintain contact with the ossicle, and
a vibration transmission element connected to the ossicular attachment element, the vibration transmission element being disposed to pass vibrations conducted from the plurality of discrete projections to an inner ear, the vibration transmission element comprising:
  a rod projecting from one end of the loop, and
  a piston coupled to and terminating an end of the rod opposite an end of the rod attached to the loop.

* * * * *